United States Patent [19]

Yakich

[11] 4,012,177
[45] Mar. 15, 1977

[54] BLOOD PUMP TUBE ELEMENT

[76] Inventor: Sam S. Yakich, 2400 Wilkinson Blvd., Apt. 329, Charlotte, N.C. 28208

[22] Filed: Aug. 31, 1973

[21] Appl. No.: 393,568

[52] U.S. Cl. ............................. 417/477; 417/478; 128/214 F

[51] Int. Cl.² ................. F04B 43/08; F04B 43/12

[58] Field of Search .......... 417/476, 477, 478, 479, 417/244, 475; 222/214; 128/214 F

[56] References Cited

UNITED STATES PATENTS

| 419,481 | 1/1890 | Lee | 417/477 |
|---|---|---|---|
| 2,527,614 | 10/1950 | Arpin | 417/479 X |
| 2,553,543 | 5/1951 | Bodine | 417/244 X |
| 3,074,351 | 1/1963 | Foster | 417/244 |
| 3,148,624 | 9/1964 | Baldwin | 417/479 X |
| 3,597,124 | 8/1971 | Adams | 417/477 |
| 3,673,924 | 7/1972 | Zakrzewski | 417/477 |
| 3,679,331 | 7/1972 | Kushner | 417/478 X |
| 3,687,580 | 8/1972 | Griffiths | 417/477 X |
| 3,720,485 | 3/1973 | Holman | 417/479 X |
| 3,749,290 | 7/1973 | Micallef | 222/214 |

*Primary Examiner*—Carlton R. Croyle
*Assistant Examiner*—Thomas I. Ross

[57] ABSTRACT

The Blood Pump Tube Element will prevent the destruction of blood cells during a prolonged pumping of blood. The device comprises a series of interconnected bag-like chambers within a tube. The chambers fully contain fluid (blood) and each is provided with inlet and outlet valve means. The tube is engaged by a plurality of rollers mounted on rotating arms, thereby giving a peristaltic pumping action to the fluid in the bag-like chambers. Additionally, the position of the rollers on the arms may be adjusted.

1 Claim, 4 Drawing Figures

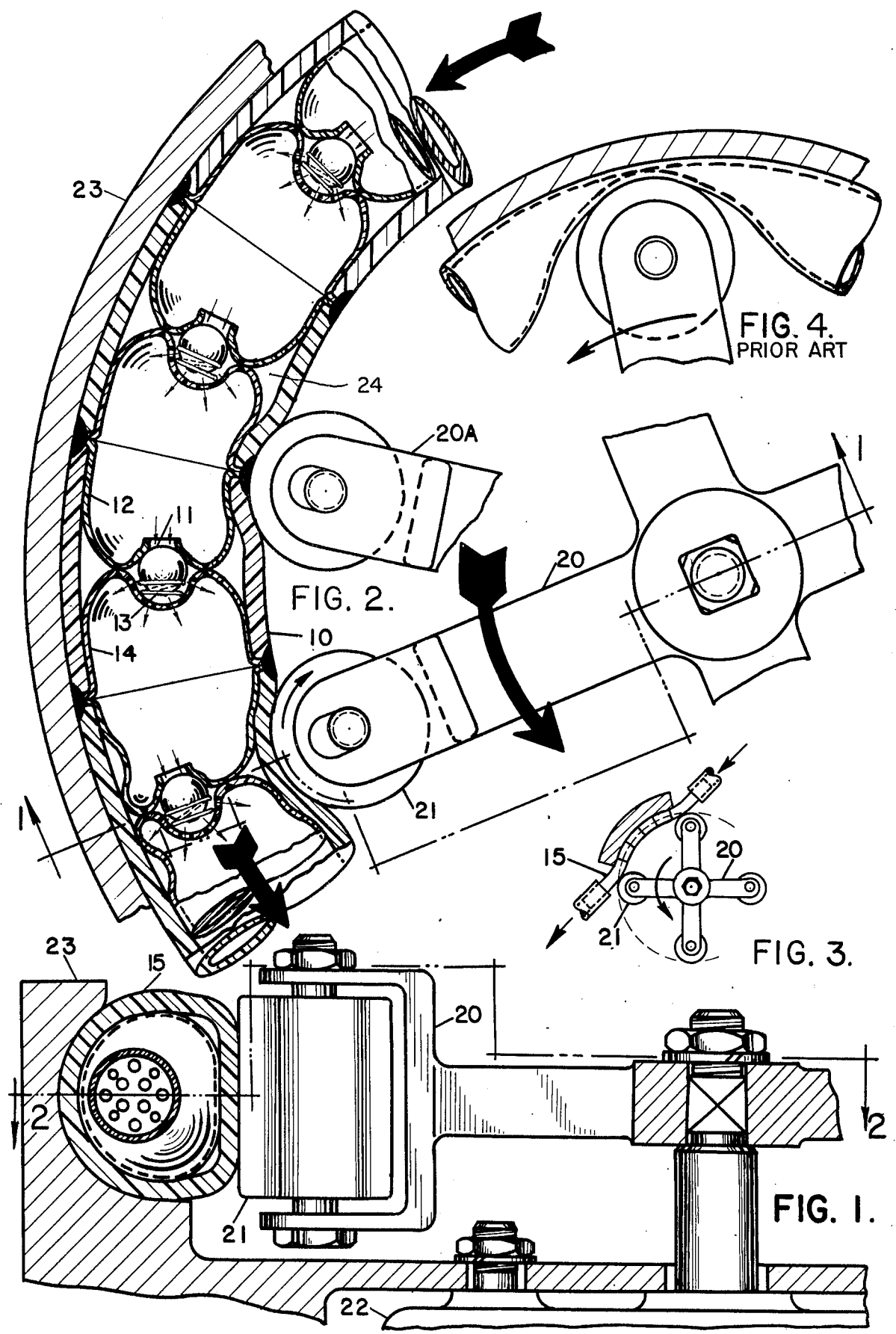

BLOOD PUMP TUBE ELEMENT

BACKGROUND OF THE INVENTION

The Blood Pump Tube Element is conceived to prevent the destruction of the human blood cells during the prolonged pumping of the blood. The destruction of the human red blood cells is known in the art of medicine as "hemolytis". It presents a major problem during long surgical operations. The development of "hemolytis" also can force kidney machine patients to go off the machine before their treatment is completed.

The red blood cells, eritrocites, are systematically destroyed due to the prolonged exposure to the physical wall pressures and the "milling" action by tube walls in the prior art pumps. The elimination of this problem called "hemolytis" by the new proposed Blood Pump Tube Element invention will make possible: extended application of kidney machine treatments and prolonged surgical operations, with mechanically unchanged blood fluid, such as open heart surgery and organ transplants.

The single wall plastic tube or the complex pumping apparatus of the present art are unable to match the simplicity, functionality, and reliability of the proposed invention.

THE BLOOD PUMP TUBE ELEMENT, IN BRIEF, THE BPTE.

BRIEF DESCRIPTION OF THE DRAWING

FIG. 1 is an elevation cross-section and the view of the BPTE 15, roller 21 and arm 20, taken in the direction of arrows 1—1 of FIG. 21.

FIG. 2 is a plane cross-section and the view of BPTE 15, rollers 21 and arm 20, taken in the direction of arrows 2—2 of FIG. 1. The same roller 21 is shown in an earlier position by the arm 20A.

FIG. 3 is a plane view of the BPTE arrangement, including the roller arms, inlet and outlet connections, and the supporting wall 23 for the BPTE.

FIG. 4 is a typical prior art tube pump.

DISCUSSION

The BPTE 15 is conceived to be used to pump human blood in medical applications such as surgical operations, kidney machines, etc. The BPTE shall be placed in a rotating-arm type pump such as indicated in FIGS. 1, 2, and 3.

The main advantage to the prior art of this new proposed BPTE improvement is that the blood fluid is being pumped in a gentle and continuous way, by only the partial squeeze of the BPTE by rollers 21. An adjustable volume/pressure feature is included. The position of rollers 21 may be adjusted by moving the rollers inward and outward in slotted holes to vary the displacement of the pump.

The prior art, as shown in FIG. 4, uses a single wall plastic tube. At the place of contact, the roller has to completely squeeze the tube walls against each other in order to pump the blood positively in the desired direction. In the prior art, the blood fluid, caught continuously in the squeeze between microstructure picks and valleys of the inner surface of the tube walls, is crushed and milled. The red blood cells, eritrocites, although of microscopic size, have been observed to be destroyed in this process during prolonged blood pumping. For many of the present surgical operations, like heart transplants and kidney machine treatments, the problem of hemolytis is acute, because the operation time for the pump may be very long in order to successfully complete these complex operations and during that time hemolytis could occur.

People knowledgeable in the art of medicine are familiar with the consequences of long applications of the present art blood pumps on the patient. The blood fluid pumps are used for the longest single daily application and accumulated time on kidney machine patients. Because the patient is accumulating "dead" eritrocites and has no way of disposing of them, there is a definite time limit when the treatment has to be stopped or the body could develop many side diseases. An urgently needed application for the BPTE is the area of human organ transplants where the blood pumping may last for many hours and although tissue rejection is the main problem, hemolytis may well be a contributory problem. Future applications of the BPTE may, allowing for modifications, appear upon the discovery of a fully successful mechanical heart.

The BPTE has remarkable mechanical simplicity which makes the BPTE disposable after each single use. The need to decontaminate some of the presently suggested complex pumps makes them less desirable for blood pumping, since this process may be time-consuming. The replacement time for a BPTE may be a few seconds versus several hours needed for the decontamination of the complex pumps.

Also, due to the simplicity of the BPTE, it has high reliability.

In a prior art attempt to reduce the problem of hemolytis, pump operators were instructed to place a calibrated gauge (0.001–0.005 inch) between the tube element wall and its supporting structure, to squeeze the tube until the inner surfaces of the tube touch each other gently and then, while keeping the roller in this position, to pull out the gauge, thus expecting the clearance of 0.001 to 0.005 inch to appear and to be maintained between inner wall surfaces of the tube element. This attempt had only partial success since the inner clearance was not always maintained due to the accumulation of tolerances in a direction to cause the full squeeze of the tube at times.

SUMMARY OF THE DISCUSSION

It is held by the inventor that the BPTE will make it possible, to pump human blood such that the pumping process will not destroy the red blood cells, eritrocites, and thus prevent the disease known as hemolytis from occurring to medical patients who will undergo the use of the blood pump equipped with the BPTE.

DESCRIPTION

FIG. 1 shows the section and the view of the BPTE taken in the direction of the arrows 1—1 of FIG. 2.

The electric motor 22 rotates four arms 20; each arm 20 carries a roller 21 whose position is radially adjustable in slots along the arm. The BPTE 15 is also shown in FIG. 1 partially squeezed by an advancing roller 21 and arm 20. The arm 20A shows an earlier position of the arm 20.

FIG. 2 shows the section and the view of the BPTE taken in the direction of arrows 2—2 of FIG. 1.

The BPTE 15 shall be fabricated from an elasto-plastic material, such as polypropylene. The BPTE 15 shall be fabricated with an outer tubular element 10 fused to inner tubular bag-like elements 12 and 14, as shown in FIG. 2. The inner bag-like elements 12 and 14 are fused together to form a cavity containing an elastic spherical ball 11 and a helical metallic spring 13. The bag-like element 12 has a single hole which is closed and opened by the ball 11 to allow the passage of blood fluid. The spring 13 presses on the ball and secures more contact area with bag-like element 12 for the ball. The other bag-like element 14 has a plurality of holes to allow free passage of the fluid from the bag 12 to the bag 14. Between the bag-like elements 12 and 14 and tube 10 is dead space 24. The several bags 12 and 14 fused together to the outer tube 10 form a sequence of chambers as is shown in FIG. 2. The outer tube 10, with thicker walls than the inner bags 12 and 14, will cause the expansion of the said bags, once the side pressure from the roller 21 is released. The rollers 21, one at a time, will roll over the BPTE 15 while partially squeezing the BPTE 15 at the place of contact. This squeeze will positively move fluid from one chamber to the next inside the outer tube 10. The balls 11 will act to close the single holes in bags 12; thus the blood is pumped in the desired direction. To allow for flexibility, as well as to allow the ball and spring assembly to yield to the side pressure of the passing roller 21 over them, the bags 12 and 14 are only fused at one circumferential strip to the outer tube 10, as shown in FIG. 2. All BPTE parts shall be manufactured from biomedically inert materials.

In summary, the process of pumping with use of the BPTE is described as follows:

An electric motor 2 imparts rotary motion to the arms 20 (FIG. 3) and to the attached four rollers 21, also free to rotate on and about their own shafts. The rollers 21, one at a time, come in contact with BPTE 15, held stationary in the support 23, and roll over the BPTE 15 while squeezing (pumping) blood fluid in the direction of its rotary motion, as shown with large arrows in FIG. 2. The portions of the BPTE 15 left free from roller 21 side pressure expand back into the free shape, thus producing the needed suction effect to fill the chambers with the fluid before the next roller 21 engages the BPTE 15.

The BPTE 15 has to be fully filled with the blood fluid for a startup of the pumping process.

I claim:

1. A Blood Pump Tube Element including:

A. a sequential plurality of resilient bag-like chambers wherein each chamber has one outlet comprising a single hole in the surface of the chamber and each chamber surface opposite to the outlet has a plurality of holes for forming an inlet; including resilient spherical balls for closing each said single hole outlet even when the balls are deformed due to side pressures since the chambers will follow the same deformation and metallic helical springs for biasing the balls against the walls of the bag-like chambers containing the outlet holes and for displacing the walls inwardly to secure more closing contact area around the balls when side pressures are applied to the balls; and wherein the plurality of said chambers being fused together so as to connect the outlet and inlet surfaces of consecutive chambers; said spring-biased balls, located inside cavities formed by chamber surfaces containing the consecutive outlet and inlet holes, acting as separating valves between the bag-like chambers, B. an outer resilient tube about the said sequential plurality of bag-like chambers fused at spots to the plurality of bag-like chambers, and C. rollers mounted at ends of arms fixed about a shaft driven by an electric motor; said rollers contacting the outer tube; said arms being provided with longitudinal slots to carry position-adjustable attachment means for the rollers, thereby enabling the adjustment of side pressure or the amount of fluid to pass through the bag-like chambers.

* * * * *